(12) United States Patent  
Komori (10) Patent No.: US 7,710,111 B2  
(45) Date of Patent: May 4, 2010

(54) NONDESTRUCTIVE INSPECTION METHOD AND DEVICE

(75) Inventor: Mochimitsu Komori, Kitakyushu (JP)

(73) Assignee: Kyushu Institute of Technology, Fukuoka (JP)

( * ) Notice: Subject to any disclaimer, the term of this patent is extended or adjusted under 35 U.S.C. 154(b) by 296 days.

(21) Appl. No.: 11/909,122

(22) PCT Filed: Aug. 8, 2006

(86) PCT No.: PCT/JP2006/304961

§ 371 (c)(1),
(2), (4) Date: Sep. 19, 2007

(87) PCT Pub. No.: WO2006/103910

PCT Pub. Date: Oct. 5, 2006

(65) Prior Publication Data

US 2009/0058406 A1    Mar. 5, 2009

(30) Foreign Application Priority Data

Mar. 25, 2005   (JP) ............................. 2005-087757

(51) Int. Cl.
*G01N 27/22* (2006.01)
*G01R 33/12* (2006.01)
(52) U.S. Cl. .................. 324/228; 324/235; 324/262
(58) Field of Classification Search ............. 324/228, 324/262, 235
See application file for complete search history.

(56) References Cited

FOREIGN PATENT DOCUMENTS

| JP | 06-294850 | 10/1994 |
|----|-----------|---------|
| JP | 07-120558 | 5/1995 |
| JP | 07-151731 | 6/1995 |
| JP | 10-25658 | 1/1998 |
| JP | 2001-194341 | 7/2001 |
| JP | 2002-077953 | 3/2002 |
| JP | 2003-185636 | 7/2003 |
| JP | 2005-003405 | 1/2005 |
| JP | 2006-177747 | 7/2006 |

*Primary Examiner*—Reena Aurora
(74) *Attorney, Agent, or Firm*—McGlew and Tuttle, P.C.

(57) ABSTRACT

The present invention nondestructively analyzes the position or corrosion state of a magnetic material present in the interior of a non-magnetic material structure. The magnetic material is magnetized from the outside of the structure, and magnetic flux density of the thus-magnetized magnetic material is measured at the outside of the structure, to thereby specify the position of the magnetic material or to analyze the corrosion state of the magnetic material. The magnetic material is magnetized in two stages. After the position of the magnetic material magnetized through first-stage magnetization is specified through measurement of magnetic flux density of the magnetic material, the magnetic material is demagnetized through application of an alternating magnetic field. After second-stage magnetization is performed at a position facing the thus-specified magnetic material position, magnetic flux density of the thus-magnetized magnetic material is measured, to thereby analyze the corrosion state of the magnetic material.

9 Claims, 4 Drawing Sheets

FIG. 1

MAGNETIZATION DEVICE

FIG. 2

MAGNETIC FLUX DENSITY MEASUREMENT

FIG. 3

REINFORCING BAR DEPTH ANALYSIS

FIG. 4

NUMBER OF TIMES OF MAGNETIZATION AND MAGNETIC FLUX DENSITY

FIG. 5

Y-AXIS COMPONENT

FIG. 6

Z-AXIS COMPONENT

NONDESTRUCTIVE INSPECTION METHOD AND DEVICE

TECHNICAL FIELD

The present invention relates to a nondestructive inspection method and apparatus for nondestructively analyzing the position or corrosion state of a magnetic material (e.g., reinforcing bar or pipe) present in the interior of a structure made of a non-magnetic material (e.g., concrete, heat-insulating material, or protective material).

BACKGROUND ART

In the field of civil engineering and construction (construction industry), a very important point for the maintenance of a concrete structure (e.g., a tunnel, a bridge, or a building) is to understand the position of corroded reinforcing bars in the concrete structure or the degree of corrosion of the reinforcing bars. However, currently, no convenient technique is available for nondestructively determining or evaluating the corrosion state of reinforcing bars in the interior of a concrete structure, and such determination or evaluation requires a long period of time and high cost.

There have been known apparatuses, including an apparatus for inspecting the state of, for example, reinforcing bars or steel frames in the interior of a concrete structure, which are magnetized by any cause (see Patent Documents 1 and 2); and an apparatus for measuring the amount of metal present (see Patent Document 3). However, these apparatuses do not actively utilize magnetization.

Thus, various methods have been employed for nondestructive inspection of a reinforced concrete structure, but most of the methods are intended to inspect deterioration of the concrete structure, or cavities, cracks, etc. which occur therein. Therefore, demand has arisen for a method for more conveniently inspecting corrosion of reinforcing bars in the interior of a concrete structure (i.e., in a special environment).

Patent Document 1: Japanese Patent Application Laid-Open (kokai) No. 2002-77953

Patent Document 2: Japanese Patent Application Laid-Open (kokai) No. 2003-185636

Patent Document 3: Japanese Patent Application Laid-Open (kokai) No. H07-151731

DISCLOSURE OF THE INVENTION

Problems to be Solved by the Invention

In view of the foregoing, an object of the present invention is to nondestructively evaluate the corrosion state of a magnetic material (e.g., reinforcing bar or pipe) in the interior of a structure made of a non-magnetic material (e.g., concrete, heat-insulating material, or protective material) by magnetizing the magnetic material and analyzing magnetic flux distribution thereof.

Means for Solving the Problems

The present invention provides a nondestructive inspection method for nondestructively analyzing the position or corrosion state of a magnetic material present in the interior of a non-magnetic material structure. This method comprises magnetizing the magnetic material from the outside of the structure, and measuring magnetic flux density of the thus-magnetized magnetic material at the outside of the structure, to thereby specify the position of the magnetic material or to analyze the corrosion state of the magnetic material.

The magnetic material is magnetized in two stages. After the position of the magnetic material magnetized through first-stage magnetization is specified through measurement of magnetic flux density of the magnetic material, the magnetic material is demagnetized through application of an alternating magnetic field. After second-stage magnetization is performed at a position facing the thus-specified magnetic material position, magnetic flux density of the thus-magnetized magnetic material is measured, to thereby analyze the corrosion state of the magnetic material.

The present invention also provides a nondestructive inspection apparatus for nondestructively analyzing the position or corrosion state of a magnetic material present in the interior of a non-magnetic material structure. The nondestructive inspection apparatus comprises a magnetization device having a function of generating a magnetic field for magnetizing the magnetic material from the outside of the structure; and a magnetic sensor for measuring, at the outside of the structure, magnetic flux density of the magnetic material magnetized by means of the magnetization device. On the basis of the thus-measured magnetic flux density, the position of the magnetic material is specified, or the corrosion state of the magnetic material is analyzed.

The magnetization device further has a function of generating an alternating magnetic field, and demagnetizes the magnetized magnetic material through application of an alternating magnetic field after the position of the magnetic material is specified through measurement of magnetic flux density thereof. The magnetization device further performs magnetization at a position facing the thus-specified magnetic material position, and the magnetic sensor measures magnetic flux density of the thus-magnetized magnetic material, to thereby analyze the corrosion state of the magnetic material.

EFFECTS OF THE INVENTION

According to the present invention, reinforcing bars, etc. in a structure can be readily and nondestructively inspected, and corroded reinforcing bars can be efficiently evaluated. Therefore, the present invention facilitates inspection of reinforcing bars, etc. in a structure in the field of civil engineering and construction (construction industry), and thus enables the period of maintenance of a structure (e.g., a tunnel, a bridge, or a building) to be estimated. According to the present invention, even when pipes are thickly covered with a heat-insulating material or a protective material, corrosion of the pipes can be inspected without removal of the heat-insulating material or protective material. In addition, pipes, etc. in the ground can be inspected without digging up the ground.

BEST MODES FOR CARRYING OUT THE INVENTION

In the present invention, a magnetic material (reinforcing bar) in the interior of a structure (e.g., a concrete structure) is magnetized; magnetic flux density of the thus-magnetized magnetic material is measured; and the corrosion state of the reinforcing bar is analyzed on the basis of the thus-obtained magnetic flux distribution. The present invention will next be described by taking, as an example, the case where the magnetic material is a reinforcing bar. However, the present invention is not limited to a solid magnetic material (e.g., a reinforcing bar), and can be employed for analysis of any "magnetizable material" (e.g., a "ferromagnetic material" or a "diamagnetic material"); for example, a hollow magnetic material such as a pipe. In addition, the present invention can be applied not only to the field of construction and civil engineering, but also to, for example, pipes used in plants or facilities, as well as pipes in the ground. The present invention will next be described by taking, as an example, the case where the structure is a concrete structure. However, the present invention can be applied to the case where the structure is made of a non-magnetic material (e.g., a heat-insulating material or a protective material) for thickly covering pipes.

For analysis of a reinforcing bar in the interior of a structure, the position of the reinforcing bar must be specified. In order to specify the reinforcing bar position, in a first step, the reinforcing bar is magnetized through application of a magnetic field for magnetization in the vicinity of a position where the reinforcing bar is estimated to be located. The resultant magnetic flux distribution is measured, and the position of the reinforcing bar is determined on the basis of the thus-measured magnetic flux distribution. This first step may be omitted in the case where the position of the reinforcing bar has been determined on the basis of, for example, a construction diagram or a previous measurement.

Subsequently, in a second step, the reinforcing bar, whose position has been determined above, is magnetized in radial directions (e.g., upward, downward, and lateral directions) about the reinforcing bar (in the below-described measurement, X is 50 cm and Z is 8 to 15 cm), and the resultant magnetic flux distribution is measured. The corrosion state of the reinforcing bar is analyzed on the basis of the magnetic flux distribution.

(Magnetization and Measurement)

Figure 1:
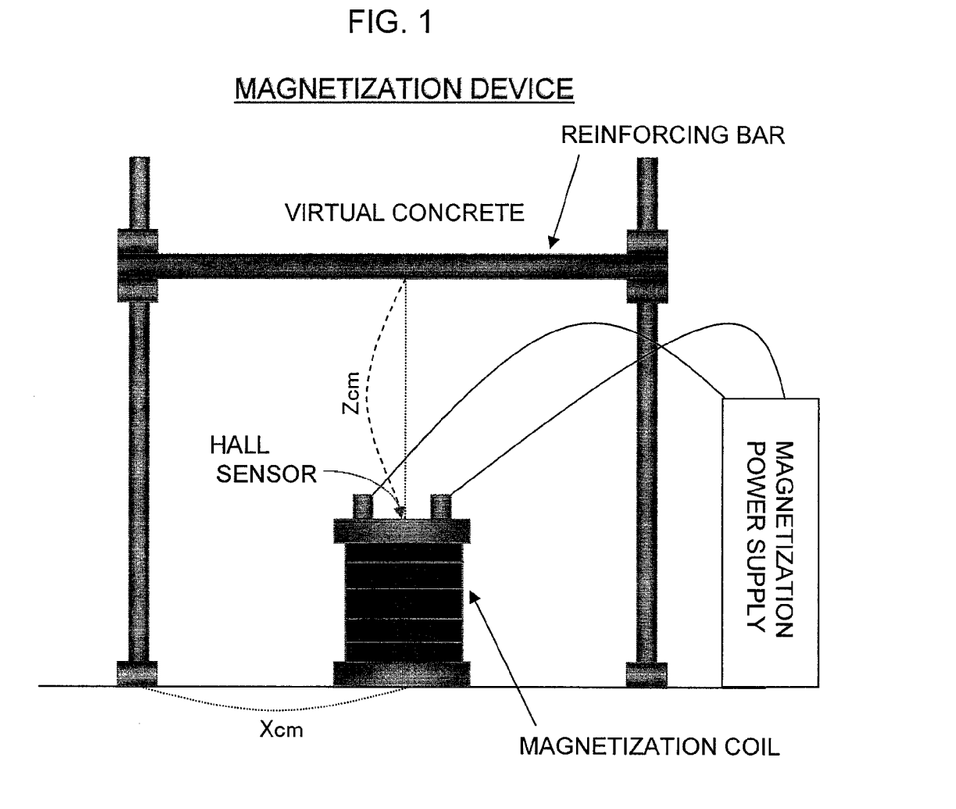
FIG. 1 is a representation showing a magnetization device.

FIG. 1 is a representation showing a magnetization device. Above the magnetization device is provided an experimental reinforcing bar simulating a reinforcing bar in a structure (virtual concrete structure shown in FIG. 1). The experimental reinforcing bar is supported at its both ends by support columns made of non-magnetic material. A magnetization power supply shown in FIG. 1 can supply a direct electric current (pulse electric current) enough to magnetize the reinforcing bar in the structure. If necessary, the power supply can supply an alternating electric current enough to generate an alternating magnetic field for demagnetizing the once-magnetized reinforcing bar. A Hall sensor is provided for measuring a magnetic field applied during magnetization, and can measure a magnetic field generated from a magnetization coil.

A coil (copper wire) of any configuration can be employed as a magnetization source of the present invention, so long as a strong magnetic field can be generated. When this coil is cooled by use of, for example, liquid nitrogen, the electric resistance of the coil is reduced to about half to one third, and electric current can be caused to flow therethrough easily with heat generation being suppressed. In the device shown in FIG. 1, a pulse electric current (e.g., a triangular waveform pulse having a duration of about 150 ms) is caused to flow, as a direct electric current, through the coil, whereby a strong magnetic field (e.g., about 5 T ($Wb/m^2$)) is generated instantaneously. When the thus-generated magnetic field is applied to an object, the object can be magnetized. The pulse magnetization method, which generates a magnetic field through instantaneous flow of electric current, can cause a large electric current to flow, and can generate a strong magnetic field. The pulse magnetization method is also advantageous in that, for example, the method realizes downsizing of the magnetization device and cost reduction, and even when the device is incorporated into an apparatus, magnetization can be performed.

A superconducting wire material may be employed for generating a strong magnetic field. When a superconducting wire material cooled by a refrigerant (e.g., liquid nitrogen) or a cryocooler is employed, the size of a coil can be reduced, since a large electric current can be caused to flow through the coil with generation of heat from the coil being suppressed. When direct electric current is caused to flow through this superconducting magnet, a strong magnetic field can be generated in a time-consistent manner. Alternatively, a pulse electric current may be applied to the superconducting magnet.

When a magnetized high-temperature superconductor (disk) is employed, a magnetic field of 10 T or more, which is higher by a factor of 10 or more than that generated by an existing magnet, can be generated constantly.

Figure 2:
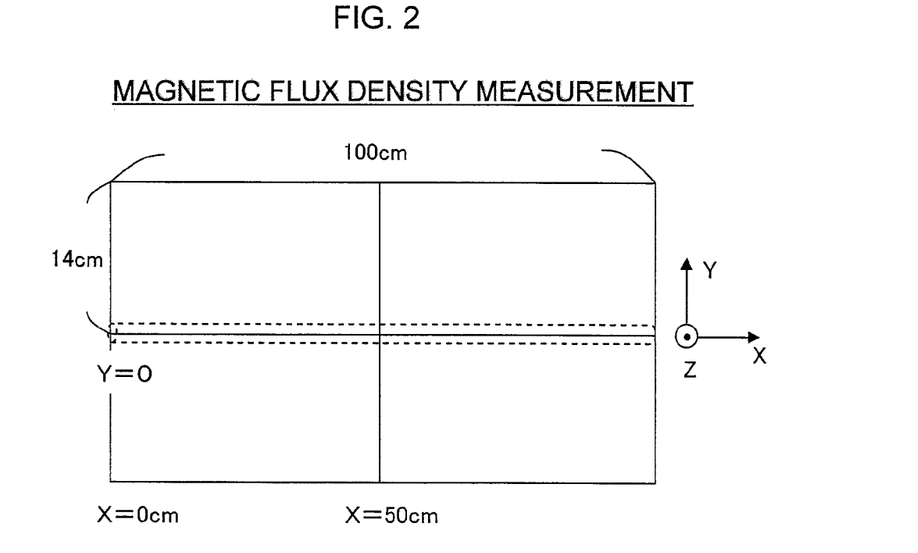
FIG. 2 is a representation for explaining measurement of magnetic flux density.

FIG. 2 is a representation for explaining measurement of magnetic flux density. In the coordinate system shown in FIG. 2, the X-axis direction corresponds to a direction parallel to a reinforcing bar; the Y-axis direction corresponds to one direction perpendicular to the X-axis direction; and the Z-axis direction corresponds to a direction perpendicular to the Y-axis direction. The thus-shown Z-axis direction is perpendicular to the sheet of FIG. 2. The origin of the X-axis is located at the left end, and the origin of the Y-axis is located directly on the reinforcing bar. Measurement data described hereinbelow (see FIGS. 5 and 6) show the distribution of magnetic flux density of a reinforcing bar having a full length of 100 cm measured such that the measurement point is changed from the X-axis center (50 cm point; the magnetization point) of the reinforcing bar in the Y-axis direction up to 14 cm at intervals of 2 cm.

In the magnetic flux distribution in the X-axis direction, the direction of magnetic flux changes at the center of the reinforcing bar (i.e., magnetization point). Specifically, magnetic flux enters the center of the reinforcing bar, and, for example, the vicinity of the center of the reinforcing bar becomes an S pole, and both ends of the reinforcing bar become N poles. This polar distribution is affected by a magnetic field generated by the magnetization coil. In the magnetic flux distribution in the Y-axis direction, the direction of magnetic flux changes at the reinforcing bar. Through this phenomenon, the position of the reinforcing bar in the Y-axis direction can be estimated. In the magnetic flux distribution in the Z-axis direction, magnetic flux density is highest at the magnetization point, and mirror-image magnetic flux distributions having mutually opposite directions are formed on both sides. The strongest magnetic flux is measured in the Z-axis direction, and the magnetic flux distribution profile in the Z-axis direction is clear as compared with that in the X- or Y-axis direction. Therefore, the magnetic flux distribution in the Z-axis direction is suitable for use in the below-described analysis of reinforcing bar corrosion.

(Analysis of Reinforcing Bar Position)

Figure 3:
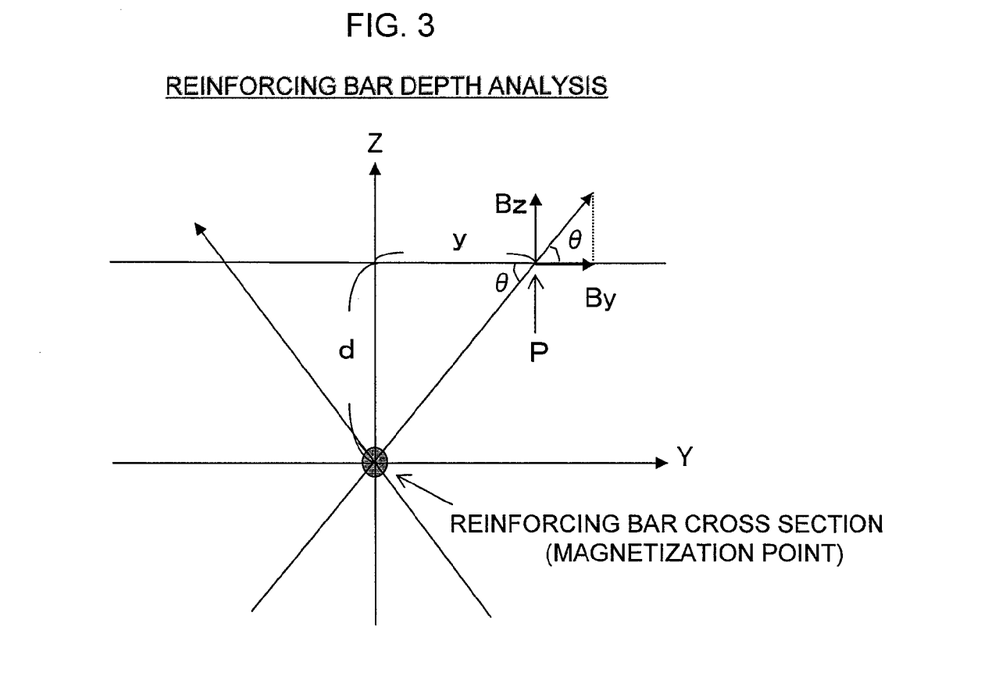
FIG. 3 is a representation for explaining analysis of reinforcing bar position.

FIG. 3 is a representation for explaining analysis of depth of a reinforcing bar. This reinforcing bar is magnetized in advance through application of a magnetic field for magnetization. Even in the case where the exact position of a reinforcing bar present in a structure fails to be specified, when, at least, magnetization is performed in the vicinity of a position where the reinforcing bar is estimated to be located, the position of the reinforcing bar can be sufficiently analyzed.

As shown in FIG. 3, it is assumed that the reinforcing bar extends in a direction perpendicular to the sheet of FIG. 3 (i.e., in the X-axis direction). The Z-axis corresponds to a direction extending upward from the reinforcing bar, and the Y-axis corresponds to a direction perpendicular to the Z-axis. As is clear from FIG. 3, the sign of the Y-axis magnetic flux density is reversed at the Z-axis. This phenomenon implies that the direction in which magnetic flux emanating radially from the reinforcing bar enters a magnetic sensor is reversed. A point at which the sign of the Y-axis magnetic flux density is reversed can be detected as being located directly above the reinforcing bar. The Y-axis direction distance y of a measurement point P, which is located the distance y away (in the Y-axis direction) from the above-detected point, can be determined through simple distance measurement.

Subsequently, a vector (component) By of magnetic flux in the Y-axis direction (i.e., Y-axis magnetic flux density) and a vector (component) Bz of magnetic flux in the Z-axis direction (i.e., Z-axis magnetic flux density) are measured at the measurement point P. The reinforcing bar is located in a direction opposite the direction of composite vector of these vectors. Therefore, when tan θ of the magnetic flux components in the Y-axis and Z-axis directions; i.e., Bz/By, is calculated, and tan θ is multiplied by the distance y as measured from the point located directly above the reinforcing bar, the depth d of the reinforcing bar can be determined by use of the following formula.

$$d = (Bz/By) \cdot y$$

Since tan θ becomes infinite as the measurement point approaches the point located directly above the reinforcing bar, the average of d values obtained through a plurality of times of measurement performed while the distance y is changed can be regarded as the depth of the reinforcing bar.

(Reinforcing Bar Corrosion Analysis)

Subsequently, the reinforcing bar whose position has been specified as described above is magnetized, followed by measurement of magnetic flux distribution. The corrosion state of the reinforcing bar is analyzed on the basis of the magnetic flux distribution. For accurate measurement of magnetic flux, firstly, the reinforcing bar (i.e., a measurement target) is demagnetized. This demagnetization is performed by generating an alternating magnetic field through application of alternating electric current to the magnetization device.

Thereafter, magnetization is performed for analysis of corrosion of the reinforcing bar. This magnetization is generally performed through the following procedure: as shown in FIG. 1, by use of the magnetization power supply, a direct electric current (pulse electric current) is supplied to the coil such that the reinforcing bar (i.e., magnetic material) present in the structure made of a non-magnetic material (e.g., concrete) is magnetized from a direction perpendicular to the reinforcing bar (e.g., from a point directly below the reinforcing bar or a point directly above the reinforcing bar). As shown in FIG. 1, when a single magnetization device is employed, generated magnetic flux enters the reinforcing bar at its center (magnetization point), which faces the magnetization device, and then passes through the reinforcing bar. Thereafter, the magnetic flux comes out of the reinforcing bar through its both ends, and returns to the opposite side of the magnetization device. Therefore, the center of the reinforcing bar is magnetized into an N (or S) pole, and the left and right ends thereof are magnetized into the counter magnetic pole. Alternatively, two or more magnetization devices may be provided on the left and right sides of the reinforcing bar in a longitudinal direction. In such a case, the reinforcing bar is magnetized by means of magnetic flux which emanates from one of the magnetization devices and enters the reinforcing bar, and which passes through the reinforcing bar and then comes out thereof toward another magnetization device.

Figure 4:
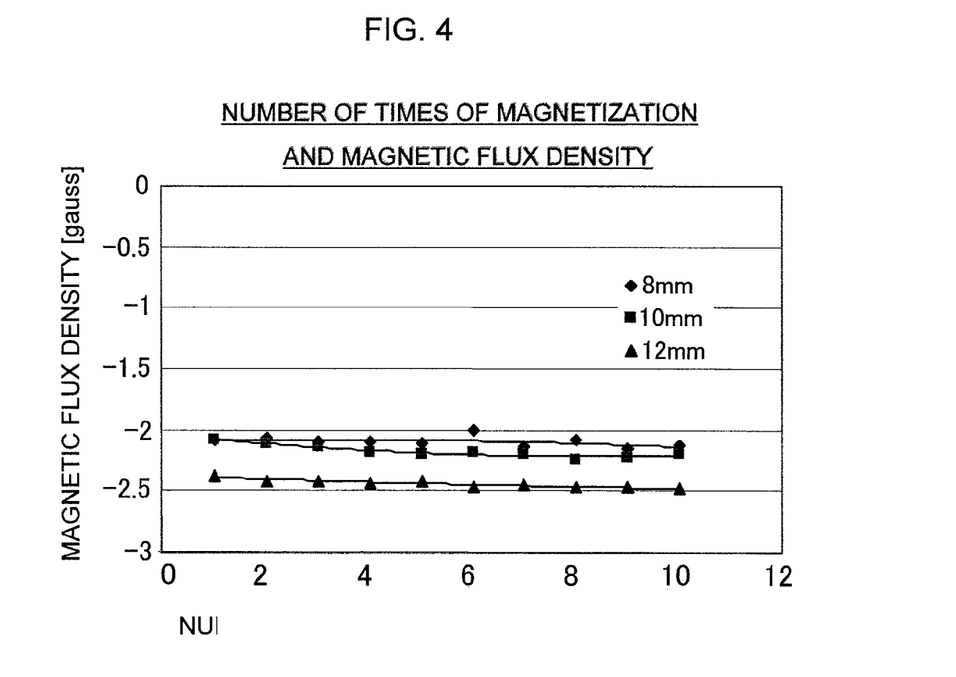
FIG. 4 is a graph showing the relation between number of times of magnetization and magnetic flux density measured for three different reinforcing bars having different diameters of 8, 10, and 12 mm under the same conditions in terms of applied magnetic field and application distance.

FIG. 4 is a graph showing the relation between number of times of magnetization and magnetic flux density measured for three different reinforcing bars having different diameters of 8, 10, and 12 mm under the same magnetization conditions in terms of, for example, applied magnetic field and application distance. As is clear from FIG. 4, magnetic flux density varies depending on reinforcing bar diameter. Therefore, measurement of magnetic flux density enables the diameter of a reinforcing bar (and thus the corrosion state of the reinforcing bar) to be estimated. For example, a reduction in diameter of a portion of a reinforcing bar due to corrosion can be determined through observation of distortion of a magnetic flux density distribution profile. That is, when the distribution profile distorts, a corroded portion can be determined to be present. When magnetic flux density measurement, which enables the diameter of a reinforcing bar to be estimated, is periodically performed under the same conditions and at the same position, change of the reinforcing bar over time can be analyzed.

As is clear from FIG. 4, when the number of times of application of a pulse magnetic field is increased, magnetic flux density is gradually increased to a small extent, resulting in remarkable change in magnetic flux density attributed to the difference in reinforcing bar diameter. Therefore, preferably, application of a magnetic field for magnetization is performed a plurality of times. Measurement data described hereinbelow in Example 3 were obtained through demagnetization (five times) and then application of a pulse magnetic field (five times).

In the present invention, individual components of a magnetic field generated from a magnetized magnetic material (a reinforcing bar, etc.) present in the interior of, for example, a concrete structure can be subjected to (image) processing, and the resultant images can be subjected to matching. Through use of the thus-visualized magnetic field distribution, the depth and corrosion state of the reinforcing bar, etc. can be estimated and evaluated. The magnetized reinforcing bar, etc. can be demagnetized through application of an alternating magnetic field, and thus the aforementioned evaluation can be performed repeatedly.

The present invention has been described by taking, as an example, the case where a single reinforcing bar is present in a structure. However, the present invention can be applied to the case where a plurality of reinforcing bars are arranged in a line, or the case where reinforcing bars are arranged in a grid pattern. Basically, such a case can be addressed by superposing distribution profiles as obtained from individual reinforcing bars.

Example 1

An example of a magnetization power supply which may be employed in the present invention can supply a direct pulse electric current (up to 20,000 A) for magnetization. In addition, the magnetization power supply can supply an alternating current (up to 7,000 A) for demagnetizing a once-magnetized reinforcing bar so that the current is gradually reduced.

A magnetic field generated varies depending on the size of a magnetization coil employed or the number of coil turns. An example of a magnetization coil (hollow core) which may be employed in the present invention has the following specification.

Inner diameter: 30 mm, outer diameter: 118 mm, height: mm, wire diameter: 1.5 mm, number of turns: 690, coil resistance: 1.20Ω (at ambient temperature), 0.5Ω (in liquid nitrogen), and bobbin material: stainless steel.

Example 2

Figure 5:
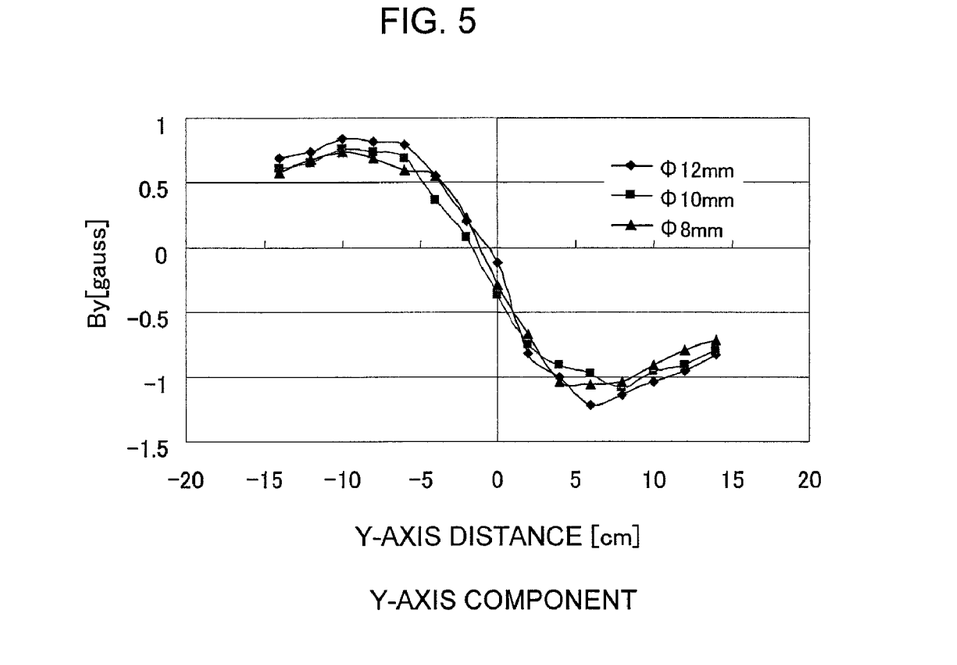
FIG. 5 is a graph showing results of measurement of a Y-axis magnetic flux component By performed for three different reinforcing bars having diameters of 8, 10, and 12 mm (reinforcing bar depth: 10 cm each), while varying the Y-axis distance.
Figure 6:
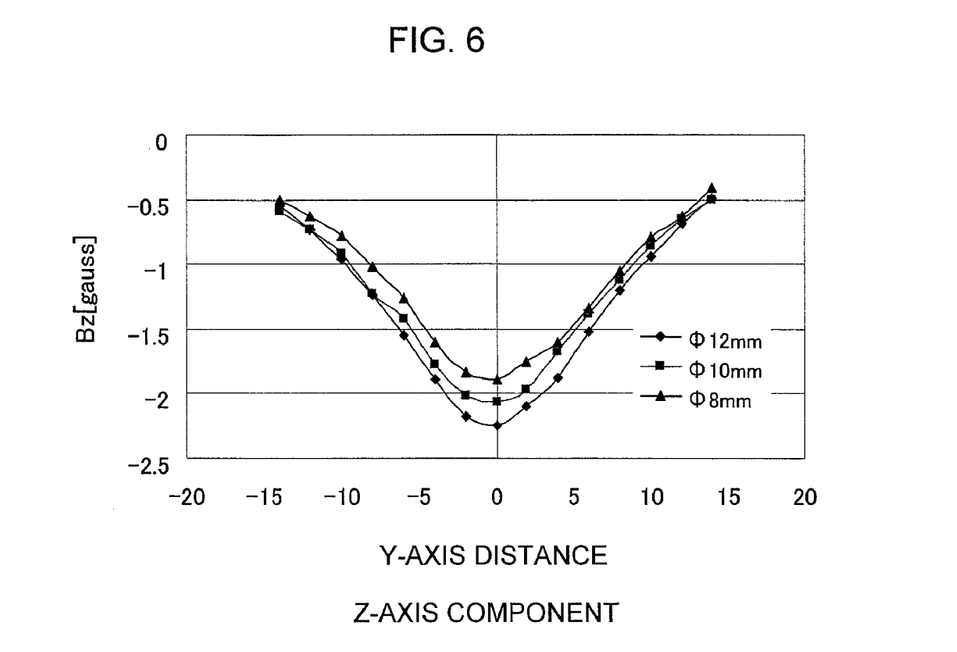
FIG. 6 is a graph showing results of measurement of a Z-axis magnetic flux component Bz performed for three different reinforcing bars having diameters of 8, 10, and 12 mm (reinforcing bar depth: 10 cm each), while varying the Y-axis distance.

FIGS. 5 and 6 are graphs respectively showing results of measurement of a Y-axis magnetic flux component By and a Z-axis magnetic flux component Bz performed for three different reinforcing bars having diameters of 8, 10, and 12 mm (reinforcing bar depth: 10 cm each) while changing the Y-axis distance. On the basis of these measurement data, reinforcing bar depth d can be determined by use of the formula: $d=(Bz/By) \cdot y$ as described above with reference to FIG. 3.

Figure 7:
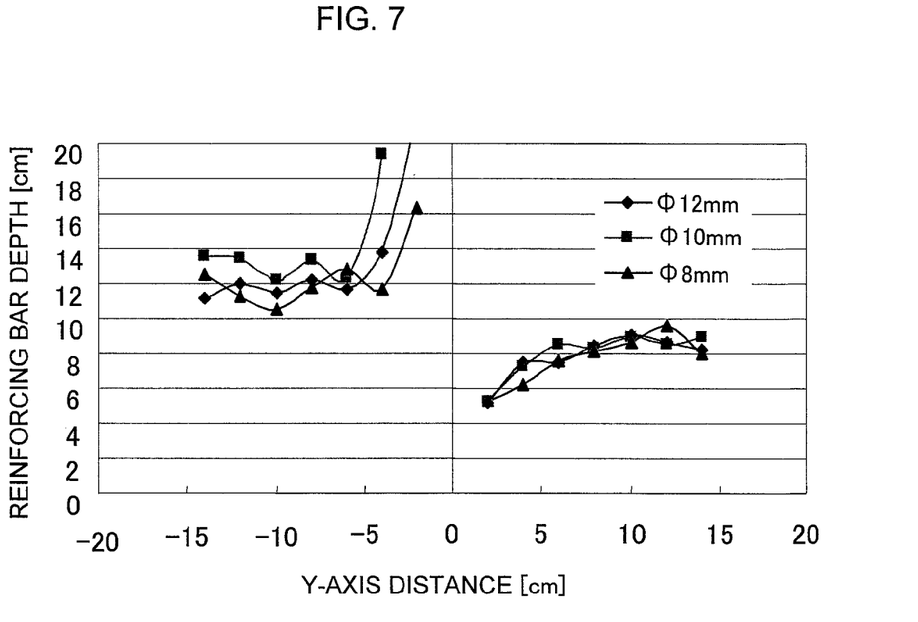
FIG. 7 is a graph showing data of determined reinforcing bar depth d.

FIG. 7 is a graph showing data of determined reinforcing bar depth d. As is clear from FIG. 7, the reinforcing bar depth is almost exactly determined to be 10 cm through magnetic flux measurement (exclusive of a region in the vicinity of a Y-axis value of zero).

Example 3

Figure 8:
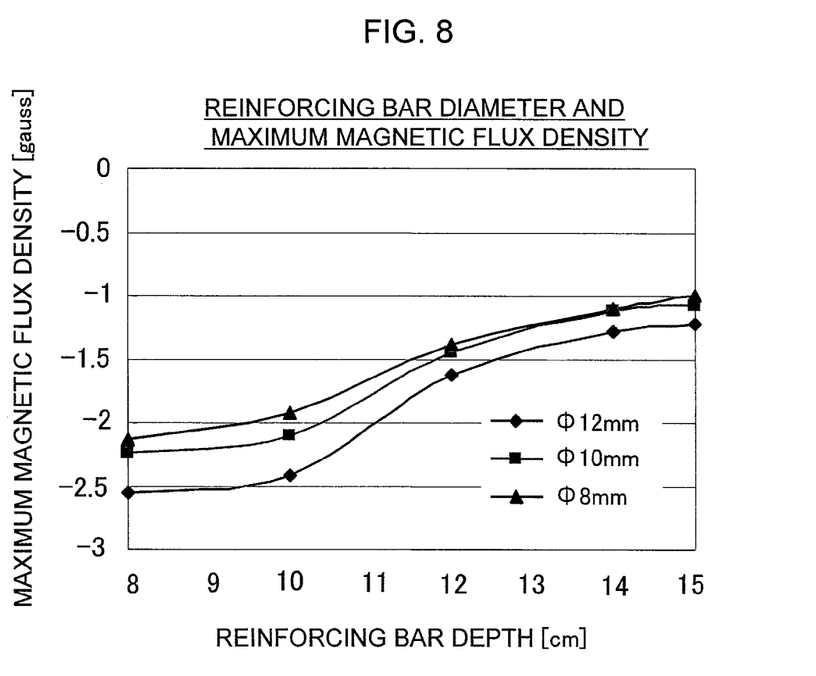
FIG. 8 is a graph showing results of measurement of maximum magnetic flux density performed for three different reinforcing bars having diameters of 8, 10, and 12 mm while changing the reinforcing bar depth.

FIG. 8 is a graph showing data of maximum magnetic flux density as measured on three different reinforcing bars having diameters of 8, 10, and 12 mm under varied reinforcing bar depths. Maximum magnetic flux density is obtained as a Z-axis magnetic flux component (Bz) at a point in a direction perpendicular to the magnetization point (i.e., in the Z-axis direction) (see FIG. 3). In other words, the maximum magnetic flux density is obtained when the magnetic flux which emanates radially from the reinforcing bar is detected as a radial-direction magnetic flux component at a point that is located outside a concrete structure and is closest to the magnetization point of the reinforcing bar. As is clear from FIG. 8, when reinforcing bar depth is small, a large difference in maximum magnetic flux density is observed between reinforcing bars of different diameters. However, the greater the reinforcing bar depth, the smaller the difference in maximum magnetic flux density. Conceivably, this phenomenon is attributed to that both a magnetic field for magnetization and a magnetic field for measurement are reduced as a result of an increase in both distance for magnetization of the reinforcing bars and distance for measurement. However, such a problem can be solved by further enhancing the magnetic field for magnetization.

Although the present invention has been described on the basis of the illustrated example, the invention is not limited to the above-described example. The present invention encompasses other modifications which may be readily made by those skilled in the art without departing from the scope of the invention as defined by the appended claims.

The invention claimed is:

1. A nondestructive inspection method for nondestructively analyzing the position or corrosion state of a magnetic material present in the interior of a non-magnetic material structure, the method comprising:
   magnetizing the magnetic material from outside of the non-magnetic material structure;
   measuring magnetic flux density of the thus-magnetized magnetic material at the outside of the structure;
   defining one direction perpendicular to the magnetic material extending in an X-axis direction as a Z-axis direction and a direction perpendicular to these directions as a Y-axis direction;
   specifying the position of the magnetic material by determining a depth of the magnetic material in the structure through calculation from components of the measured magnetic flux density in the Y-axis direction and the Z-axis direction; and
   measuring the magnetic flux density of the magnetic material whose position has been specified, and measuring, in the vicinity of a magnetization point, maximum magnetic flux density which varies depending on a diameter of the magnetic material, to thereby analyze the corrosion state.

2. A nondestructive inspection method according to claim 1, wherein the magnetic material is magnetized in two stages; after the position of the magnetic material magnetized through first-stage magnetization is specified through measurement of magnetic flux density of the magnetic material, the magnetic material is demagnetized through application of an alternating magnetic field thereto; and after second-stage magnetization is performed at a position facing the thus-specified magnetic material position, magnetic flux density of the thus-magnetized magnetic material is measured, to thereby analyze the corrosion state of the magnetic material.

3. A nondestructive inspection method according to claim 1, wherein the non-magnetic material structure is made of concrete, heat-insulating material, or protective material; and the magnetic material is reinforcing bar or pipe.

4. A nondestructive inspection method according to claim 1, wherein the magnetization is performed by means of a pulse magnetic field generated by causing a pulse electric current to flow through a coil; a magnetic field generated by a superconducting magnet employing a superconducting wire material; or a magnetic field constantly generated by a magnetized superconductor.

5. A nondestructive inspection apparatus for nondestructively analyzing the position or corrosion state of a magnetic material present in the interior of a non-magnetic material structure, the apparatus comprising:
   a magnetization device having a function of generating a magnetic field for magnetizing the magnetic material from outside of the non-magnetic material structure; and
   a magnetic sensor for measuring, at the outside of the structure, magnetic flux density of the magnetic material magnetized by means of the magnetization device, wherein:

one direction perpendicular to the magnetic material extending in an X-axis direction is defined as a Z-axis direction and a direction perpendicular to these directions is defined as a Y-axis direction;

the position of the magnetic material is specified by determining a depth of the magnetic material in the structure through calculation from components of the measured magnetic flux density in the Y-axis direction and the Z-axis direction; and the magnetic flux density of the magnetic material whose position has been specified is measured, and maximum magnetic flux density which varies depending on a diameter of the magnetic material is measured in the vicinity of a magnetization point to thereby analyze the corrosion state.

6. A nondestructive inspection apparatus according to claim 5, wherein the magnetization device further has a function of generating an alternating magnetic field, and demagnetizes the magnetized magnetic material through application of an alternating magnetic field after the position of the magnetic material is specified through measurement of magnetic flux density thereof the magnetization device further performs magnetization at a position facing the thus-specified magnetic material position; and the magnetic sensor measures magnetic flux density of the thus-magnetized magnetic material, to thereby analyze the corrosion state of the magnetic material.

7. A nondestructive inspection apparatus according to claim 5, wherein the non-magnetic material structure is made of concrete, heat-insulating material, or protective material; and the magnetic material is reinforcing bar or pipe.

8. A nondestructive inspection apparatus according to claim 5, wherein the magnetization device performs magnetization by means of a pulse magnetic field generated by causing a pulse electric current to flow through a coil; a magnetic field generated by a superconducting magnet employing a superconducting wire material; or a magnetic field constantly generated by a magnetized superconductor.

9. A nondestructive inspection apparatus according to claim 5, further comprising a plurality of magnetization devices arranged in a longitudinal direction of the magnetic material.

* * * * *

UNITED STATES PATENT AND TRADEMARK OFFICE
CERTIFICATE OF CORRECTION

PATENT NO. : 7,710,111 B2 Page 1 of 1
APPLICATION NO. : 11/909122
DATED : May 4, 2010
INVENTOR(S) : Mochimitsu Komori It is certified that error appears in the above-identified patent and that said Letters Patent is hereby corrected as shown below:

On the title page, item [22] should read
-- PCT Filed: March 14, 2006 --.

Signed and Sealed this

Thirty-first Day of August, 2010

David J. Kappos
*Director of the United States Patent and Trademark Office*